US006566328B1

(12) United States Patent
Rosen et al.

(10) Patent No.: US 6,566,328 B1
(45) Date of Patent: *May 20, 2003

(54) HUMAN GROWTH HORMONE

(75) Inventors: Craig A. Rosen, Laytonsville, MD (US); Timothy A. Coleman, Gaithersburg, MD (US); Mark D. Adams, North Potomac, MD (US); Jeannine D. Gocayne, Silver Spring, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/411,657

(22) Filed: Oct. 4, 1999

Related U.S. Application Data

(62) Division of application No. 08/710,324, filed on Sep. 16, 1996, now Pat. No. 5,962,411, which is a division of application No. 08/187,756, filed on Jan. 27, 1994, now Pat. No. 5,597,709.

(51) Int. Cl.[7] .................. A01N 37/18; A61K 38/00; A61K 38/27; C07H 21/02
(52) U.S. Cl. .................. 514/12; 530/399; 536/23.51
(58) Field of Search .................. 435/69.1, 69.4, 435/91.5, 252.3, 320.1, 325; 514/12; 536/23.1, 23.51; 530/399

(56) References Cited

U.S. PATENT DOCUMENTS

| | | | |
|---|---|---|---|
| 3,565,987 A | 2/1971 | Schuurs | 424/12 |
| 4,446,235 A | 5/1984 | Seeburg | 435/901.51 |
| 4,670,393 A | 6/1987 | Seeburg | 435/325 |
| 4,816,439 A | 3/1989 | Jorgensen | 514/12 |
| 5,597,709 A | 1/1997 | Seeburg | 435/91.5 |
| 5,962,411 A | * 10/1999 | Rosen et al. | 435/69.4 |

FOREIGN PATENT DOCUMENTS

| | | |
|---|---|---|
| GB | 2091739 | 8/1982 |
| WO | 93/08292 | 4/1993 |

OTHER PUBLICATIONS

Bowie et al. (1990) Science 247:1306–1310.
Brinster et al. (1984) Phil. Trans. R. Soc. Lond. 307:309–312.
Cooke et al. (1988) J. Biol. Chem. 263:9001–9006.
Cooke et al. (1988) J. Clin. Invest. 82:270–275.
Denoto et al. (1981) Nucl. Acids. Res. 9:3719–3730.
Estes et al. (1994) ACTA Paediatr. Suppl. 399:42–47.
Estes et al. (1992) J. Biol. Chem. 267:14902–14908.
Estes et al. (1990) J. Biol. Chem. 265:19863–19870.
Fiddes et al. (1979) Biochem. 76:4294–4298.
Lecomte et al. (1987) Nucl. Acids. Res. 15:6331–6348.
Lewin et al. (1985) Genes II, p. 681.
Martial et al. (1979) Science 205–602–607.
Masuda et al. (1988) Biochimica (49:125–131.
Nickel et al. (1993) Mol. Cell. Endocrin. 91:159–166.
Nickel et al. (1990) Endocrinology 126:971–976.
Ngo et al. The Protein Folding Problem and Tertiary Structure Prediction, Mertz et al., eds., Birkhauser, Boston, (1994) pp. 492–495.
Nishikawa et al. (1989) Protein Engr. 3:49–53.
Ray et al. (1990) J. Biol. Chem. 265:7939–7944.
Roskam et al. (1979) Nuc. Acids. Res. 7:305–319.
Schlesinger et al., Macromolecular Sequencing and Synthesis, Alan R. Liss, Inc., New York, (1988) pp. 127–149.
Uchida et al. (1990) Bioch. & Biophys. Res. Comm. 172:357–363.

* cited by examiner

*Primary Examiner*—John Ulm
*Assistant Examiner*—Olga N. Chernyshev
(74) *Attorney, Agent, or Firm*—Human Genome Sciences, Inc.

(57) ABSTRACT

The present invention relates to a method of treatment of patients by administration of human growth hormone. Also disclosed are DNA (or RNA) polynucleotide sequences that encode naturally occurring splice variants of human growth hormone, hGHV-2(88) and hGV-3(53), as well as analogs and derivatives thereof, which both lack nucleotide sequences normally present in the gene which codes for wild-type human growth hormone. The growth hormone variants of the present invention are of human origin and are useful for diagnostic, preventive and therapeutic purposes with respect to certain human diseases. Also disclosed is a method for producing the human growth hormone variants of the present invention by recombinant DNA techniques, as well as a method for generating antibodies directed against (and therefore inhibiting the activity of) wild-type growth hormone.

41 Claims, 10 Drawing Sheets

FIG. 2A hGHwt
-26
```
  M   A   A   G   S   R   T   S   L   L   L   A   F
  ATG GCT GCA GGC TCC CGG ACG TCC CTG CTC CTG GCT TTT-->
   1
  F   P   T   I   P   L   S   R   L   F   D   N   A
  TTC CCA ACC ATT CCC TTA TCC AGG CTT TTT GAC AAC GCT-->
              32
  T   Y   Q   E   F   E   E   A   Y   I   P   K   E
  ACC TAT CAG GAG TTT GAA GAA GCC TAT ATC CTG AAG GAG-->
  C   F   S   E   S   I   P   T   P   S   N   R   E
  TGC TTC TCA GAG TCT ATT CCA ACA CCT TCC AAC AGG GTG-->
  S   L   L   L   I   Q   S   W   L   E   P   V   Q
  TCC CTG CTC CTC ACT CAG TCA TGG CTG GAG CCC GTG CAG-->
  A   S   D   S   N   V   Y   D   L   L   K   D   L
  GCC TCG GAC AGC AAC GTC TAT GAC CTC CAC AAG GAC CTA-->
  G   S   P   R   T   G   Q   I   F   K   Q   T   Y
  GGC AGC CCC CGG ACT GGG CAG ATC TTC AAT CAG TCC TAC-->
  L   K   N   Y   G   L   L   Y   C   F   R   K   D
  CTC AAG AAC TAC GGG CTG CTC TAC TGC TTC AGG AAG GAC-->
              191
  R   S   V   E   G   S   C   G   F
  CGC TCT GTG GAG GGC AGC TGT GGC TTC TAG
```

FIG. 2C hGHV-2(88)

```
    -26
     M   A   A   G   S   R   T   S   L   L   L   A   F
    ATG GCT GCA GGC TCC CGG ACG TCC CTG CTC CTG GCT TTT→

1
     F   P   T   I   P   L   S   R   L   F   D   N   A
    TTC CCA ACC ATT CCC TTA TCC AGG CTT TTT GAC AAC GCT→

32
     T   Y   Q   E   F                                  ...→
    ACC TAT CAG GAG TTT ...

C   F   S   E   S   I   P   T   P   S   N   R   E
    TGC TTC TCA GAG TCT ATT CCA ACA CCT TCC AAC AGG GTG→

S   L   L   L   I   Q   S   W   L   E   P   V   Q
    TCC CTG CTC ACT CAG TCA TGG CTG GAG CCC GTG CAG→

A   S   D   S   N   V   Y   D   L   L   K   D   L
    GCC TCG GAC AGC AAC GTC TAT GAC CTC CAC CTG AAG GAC CTA→

G   S   P   R   T   G   Q   I   F   K   Q   T   Y
    GGC AGC CCC CGG ACT GGG CAG ATC TTC AAT CAG TCC TAC→

L   K   N   Y   G   L   L   Y   C   F   R   K   D
    CTC AAG AAC TAC GGG CTG CTC TAC TGC TTC AGG AAG GAC
                                    172
                                     F
     R   S   V   E   G   S   C   G   F
    CGC TCT GTG GAG GGC AGC TGT GGC TTC TAG
```

FIG. 2D

```
                                                                      -1
        G   L   L   C   L   L   S   W   L   Q   E   G   S   A
γ┌── GGC CTG CTC TGC CTG CTG TCC TGG CTT CAA GAG GGC AGT GCC

S   L   R   A   H   R   L   H   Q   L   A   F   D
γ┌── ATG CTC CGC GCC CGT CGC CTG TAC CAG CTG GCA TAT GAC

52
                                                                       S   L
γ┌── ... ... ... ... ... ... ... ... ... ... ... ... TCC CTC

73
        E   T   Q   Q   K   S   N   L   E   L   L   R   I
γ┌── AAA ACG CAG CAG AAA TCT AAC CTA GAG CTG CTC CGC ATC

F   L   R   S   V   F   A   N   S   L   V   Y   G
γ┌── CTC CTC AGG AGC GTC TTC GCC AAC AGC CTG GTG TAT GGC
 └─
        E   E   G   I   Q   T   L   M   G   R   L   E   D
γ┌── GAG GAA GGC ATC CAA ACG CTG ATG TGG AGG CTG GAA GAT
 └─
        S   K   F   D   T   N   K   S   H   N   D   A   L
γ┌── AGC AAG TTT GAC ACA AAC AAA TCG CAC AAC GAT GCA GAT
 └─
        M   D   K   V   E   T   F   L   R   I   V   Q   C
γ┌── ATG GAC AAG GTC GAG ACA TTC CTG CGC ATC GTG CAG TGC
```

FIG. 2E hGHV-3(53)

```
-26
 M   A   A   G   S   R   T   S   L   L   L   A   F
ATG GCT GCA GGC TCC CGG ACG TCC CTG CTC CTG GCT TTT→

1
 F   P   T   I   P   L   S   R   L   F   D   N   A
TTC CCA ACC ATT CCC TTA TCC AGG CTT TTT GAC AAC GCT→

32
 T   Y   Q   E   F   ...                            →
ACC TAT CAG GAG TTT ...

... S . L . L . I . Q . S . W . L . E . P . V . Q →
 ... TCC CTG CTC ACT CAG TCA TGG CTG GAG CCC GTG CAG→
      A   S   D   S   N   V   Y   T   C   A   G   L →
     GCC TCG GAC AGC AAC GTC TAT CGC CAC CTG AAG GAC→
      A   S   D   S   N   V   Y   T   C   A   G   L →

G   S   P   R   T   G   Q   I   F   K   Q   T   Y →
     GGC AGC CCC CGG ACT GGG CAG ATC TTC AAT CAG TCC TAC→
      L   K   N   Y   G   L   L   Y   C   F   R   K   D →
     CTC AAG AAC TAC GGG CTG CTC TAC TGC TTC AGG AAG GAC→

151
 R   S   V   E   G   S   C   G   F
CGC TCT GTG GAG GGC AGC TGT GGC AGC TTC TAG
```

FIG. 2F

```
        G   L   L   C   L   L   S   W   L   Q   E   G   S   A
                                                            -1
    ┌-GGC CTG CTC TGC CTG CTG TCC TGG CTT CAA GAG GGC AGT GCC
    └┐
     ┘

S   L   R   A   H   R   L   H   Q   L   A   F   D
    ┌-ATG CTC CGC GCC CGT CGC CTG TAC CAG CTG GCA TAT GAC
    └┐
     ┘

┌- ...   ...   ...   ...   ...   ...   ...
    └┐
     ┘
                73
                 N   L   E   L   L   R   I
    ┌- ... AAC CTA GAG CTG CTC CGC ATC
    └┐
     ┘

F   L   R   S   V   F   A   N   S   L   V   Y   G
    ┌-CTC CTC AGG AGC GTC TTC GCC AAC AGC CTG GTG TAT GGC
    └┐
     ┘
        E   E   G   I   Q   T   L   M   G   R   L   E   D
    ┌-GAG GAA GGC ATC CAA ACG CTG ATG TGG AGG CTG GAA GAT
    └┐
     ┘
        S   K   F   D   T   N   S   H   N   D   D   A   L
    ┌-AGC AAG TTT GAC ACA AAT TCG CAC AAC GAT GAC GCA CTG
    └┐
     ┘
        M   D   K   V   E   T   F   L   R   I   V   Q   C
    ┌-ATG GAC AAG GTC GAG ACA TTC CTG CGC ATC GTG CAG TGC
    └┐
     ┘
```

HUMAN GROWTH HORMONE

This application is a Divisional of and claims priority under 35 U.S.C. §120 to U.S. patent application Ser. No. 08/710,324, filed Sep. 6, 1996 (now U.S. Pat. No. 5,962,411, issued on Oct. 5, 1999), which is a Divisional of and claims priority under 35 U.S.C. §120 to U.S. patent application Ser. No. 08/187,756, filed Jan. 27, 1994 (now U.S. Pat. No. 5,597,709, issued Jan. 28, 1997), both of which are hereby incorporated by reference in their entirety.

BACKGROUND

This invention relates to newly identified polynucleotide sequences, polypeptides encoded by such sequences, the use of such polynucleotides and polypeptides, as well as the production of such polynucleotides and polypeptides. More particularly, the polypeptides of the present invention are naturally occurring splice variants of human growth hormone, hGHV-2(88) and hGHV-3(53). The invention also relates to inhibiting the action of such polypeptides.

Human growth hormone is produced in and released from the pituitary gland. hGHwt is a peptide hormone having several useful functions. One characteristic activity of human growth hormone is that it directs linear bone growth. Human growth hormone also has lactogenic activity and has been shown to be involved in metabolic processes such as lipid, nitrogen and carbohydrate metabolism. Recent studies on human growth hormone have begun to suggest that different regions of the molecule might be involved in controlling the above stated activities. Other indications of human growth hormone include its use in the treatment of hip fractures in the elderly, chronic renal insufficiency, Turner's syndrome, cancer and HIV infection and its subsequent effects.

Considerable effort has been expended in studying the human growth hormone molecule and its interaction with other cells and organs of the human body in an attempt to regulate human growth hormone's effect on these particular targets in the human body. For example, wild-type human growth hormone (hGHwt) is presently used to treat hypopituitism where not enough human growth hormone occurs naturally. Accordingly, a means by which to stimulate the natural production of human growth hormone in hypopituitism or to compete with the receptor sites of human growth hormone when a patient is subjected to hyperpituitism would be of great value, particularly in light of the fact that certain growth abnormalities are capable of being diagnosed prenatally.

Means and methods for production of human growth hormone variant proteins and to the determination of their DNA sequences and amino acid sequence of 191 amino acids by recombinant DNA technology were disclosed in U.S. Pat. No. 4,670,393 issued to Seeburg on Jun. 2, 1987, however, hitherto the present invention, there has not been disclosed two naturally occurring spliced variants of the human growth hormone polypeptide.

In one aspect of the present invention, there is provided polynucleotide DNA (or RNA) sequences encoding for naturally occurring splice variants of the human growth hormone, hGHV-2(88) and hGHV-3(53), as well as analogs and derivatives thereof, which both lack nucleotide sequences normally present in the gene which encodes for hGHwt.

In accordance with another aspect of the present invention, there is provided polypeptides which are naturally occurring splice variants of the human growth hormone, hGHV-2(88) and hGHV-3(53) which can function as an agonist and/or an antagonist for human growth hormone, as well as analogues and derivatives thereof.

In accordance with still another aspect of the present invention, there is provided a procedure for producing such polypeptide variants by recombinant DNA techniques.

In accordance with yet a further aspect of the present invention, there is provided a process for utilizing such polypeptides, or DNA sequences encoding such polypeptides for therapeutic purposes, for example stimulating the action of wild-type hGH and for inhibiting the action of wild-type hGH.

In accordance with yet another aspect of the present invention, there is provided a composition which is employed as an antagonist to such polypeptide, e.g., an antibody against such polypeptide. For example, in the treatment of hyperpituitism.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIGS. 2A and 2B collectively show the nucleotide (SEQ ID NO:1) and amino acid (SEQ ID NO:4) sequences of the wild-type hGH. FIGS. 2C and 2D collectively show the nucleotide (SEQ ID NO:2) and amino acid (SEQ ID NO:5) sequence corresponding to hGHV-2(88). FIGS. 2E and 2F collectively show the nucleotide (SEQ ID NO:3) and amino acid (SEQ ID NO:6) sequence of hGHV-3(53).

DESCRIPTION OF THE INVENTION

In accordance with another aspect of the present invention, there are provided polynucleotides which encode either the same polypeptide as the polynucleotide of the cDNA clone deposited as ATCC deposit number 75600 deposited on Nov. 3, 1993 or the cDNA clone deposited as ATCC deposit number 75601, deposited on Nov. 3, 1993 (both clones being deposited with the American Type Culture Collection, 10801 University Boulevard, Manassas, Va. 20110-2209, USA), and/or fragments, analogs, derivatives or allelic variants of such polynucleotides.

Figure 2B:
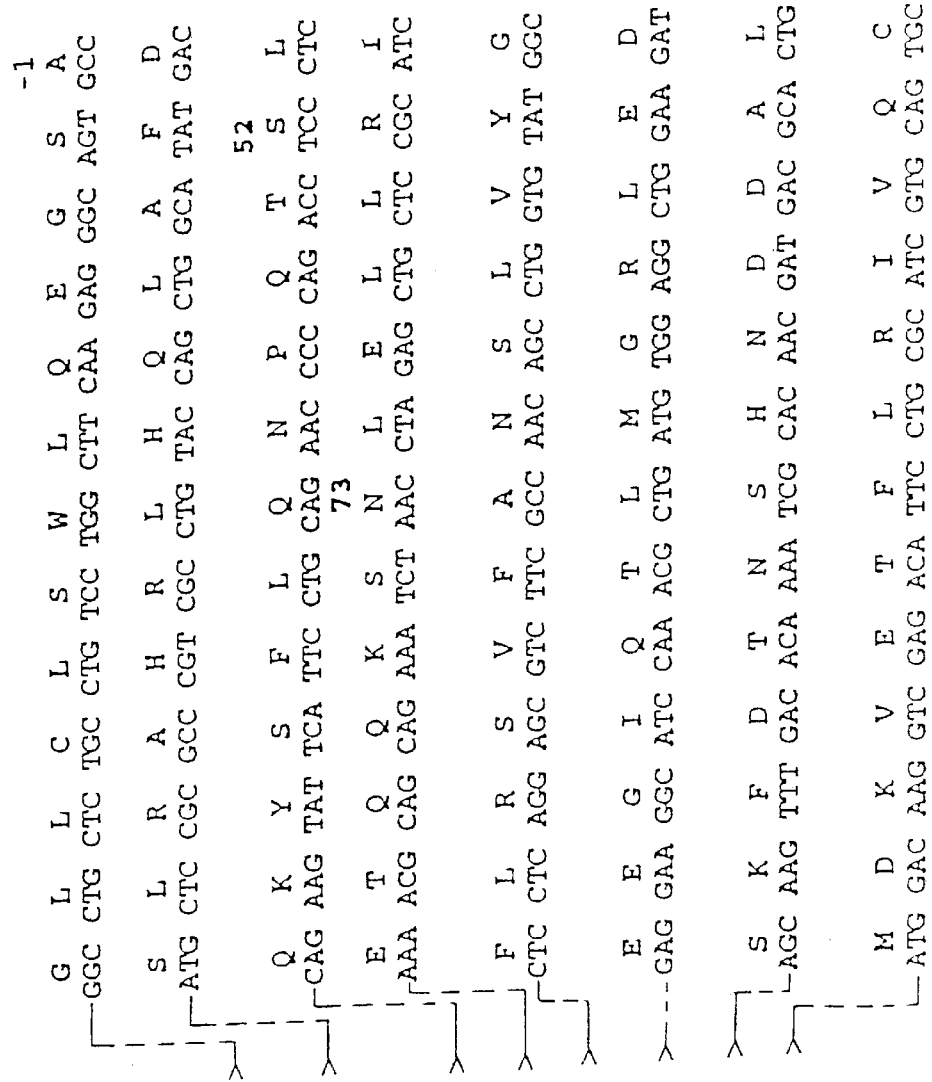
Figure 3:
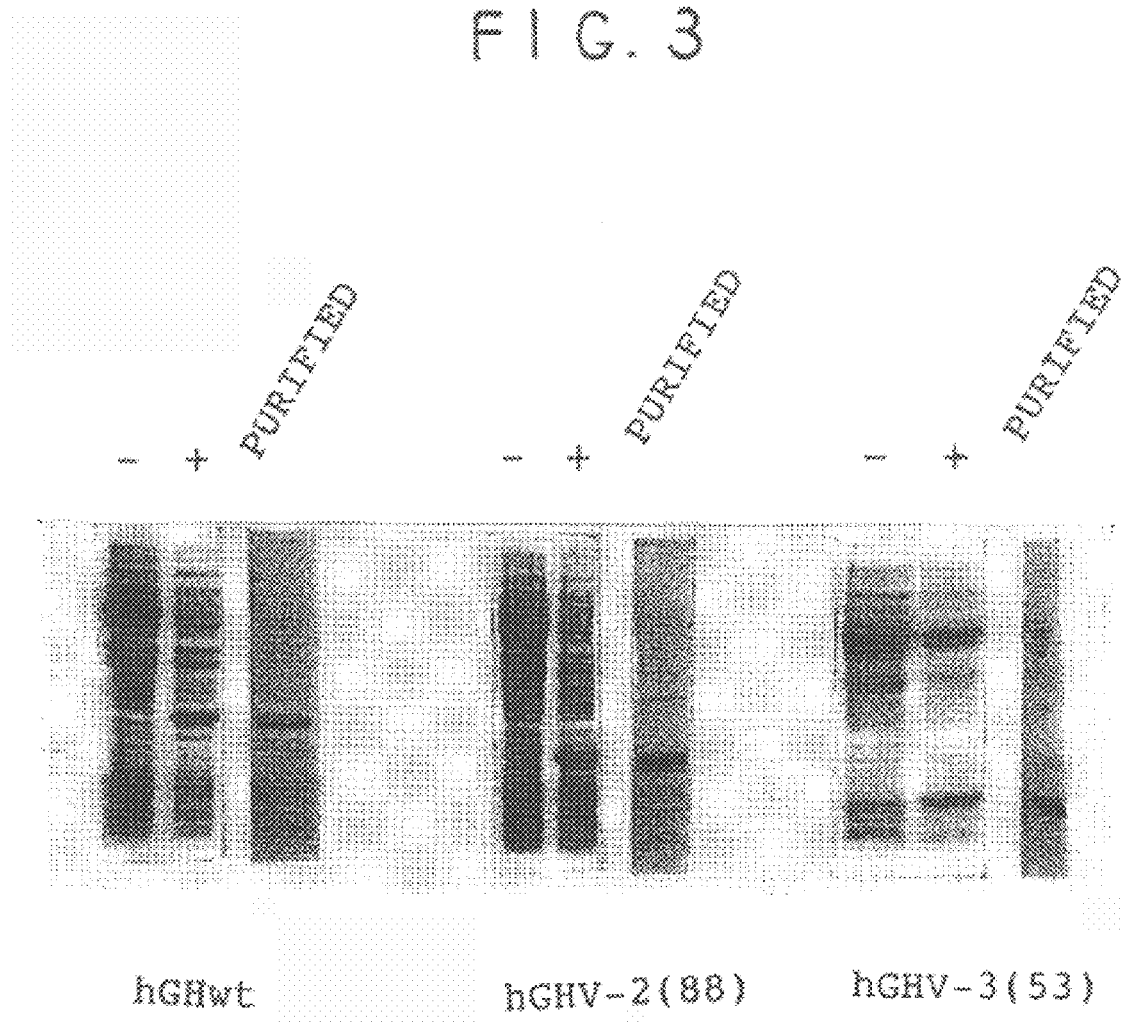
FIG. 3 illustrates bacterial expression and purification of clones containing the coding sequences for wild-type hGH, hGHV-2(88) and hGHV-3(53).
Figure 4:
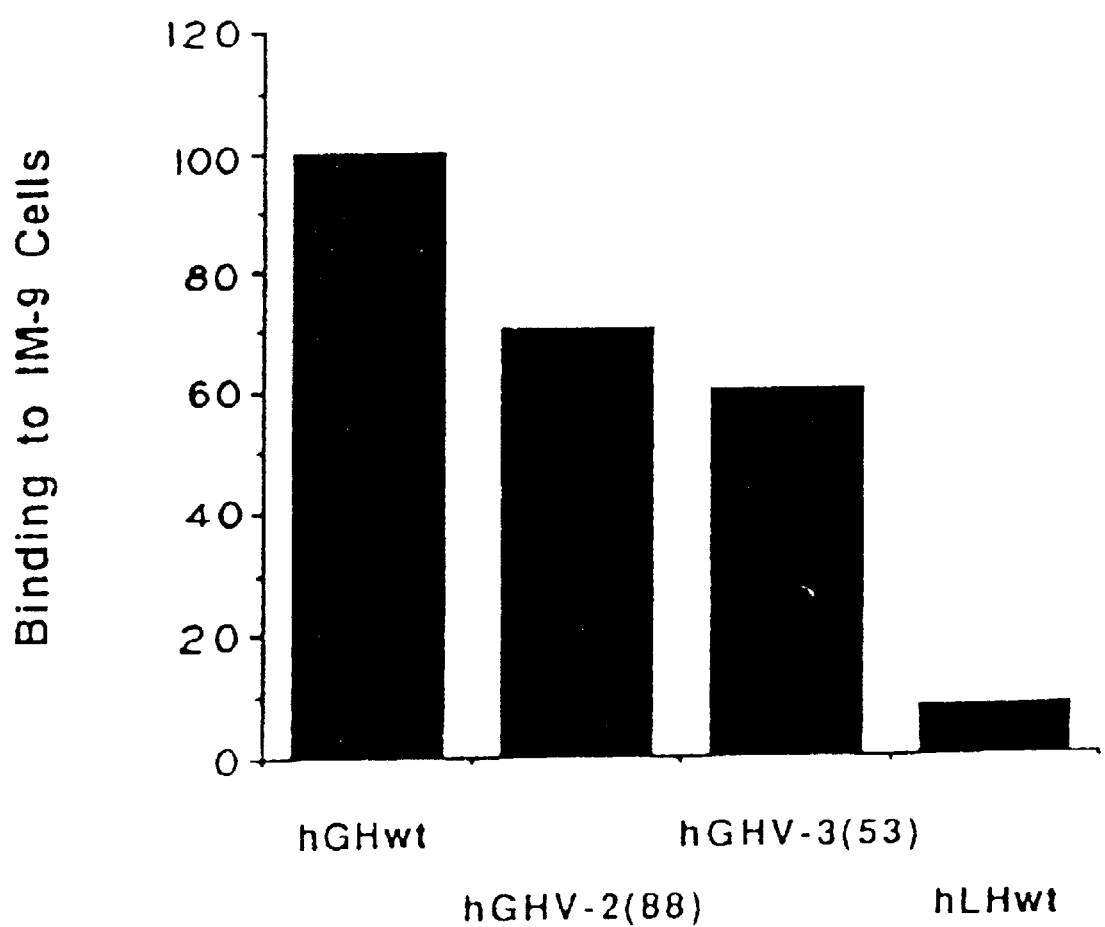
FIG. 4 illustrates the ability of the purified proteins shown in FIG. 3 to bind to hGH receptors normally present on IM-9 cells.

In the case of DNA, DNA may be single stranded or double stranded, and if single stranded the DNA sequence may be the "sense" strand shown in FIG. 2 or the one complementary thereto.

The polynucleotides (DNA or RNA, preferably DNA) include at least the portion coding for the polypeptides, which coding portion may be the same as that in the deposited clones or may be different than that in the deposited clones provided that it encodes for the same polypeptides or any allelic variants thereof. The coding portion preferably encodes at least the mature form of the polypeptides of the present invention.

The present invention further relates to polynucleotide sequences which hybridize to the hereinabove-described polynucleotide sequences if there is at least 50% and preferably 70% identity between the sequences. In another preferred embodiment the present invention relates to polynucleotide sequences which hybridize under stringent conditions to the hereinabove-described polynucleotide sequences. As herein used, the term "stringent conditions" means hybridization will occur if there is at least 95% and preferably at least 97% identity between the segments. Thus, the present invention includes DNA (RNA) sequences encoding allelic variant forms of the peptide encoded by the DNA of FIG. 1. Thus, the present invention provides isolated DNA (RNA) encoding for naturally occurring human polypeptides which are a human growth hormone and human growth hormone antagonist respectively, as well as allelic variants thereof. The DNA (RNA)is preferably provided in a purified and isolated form.

Figure 1:
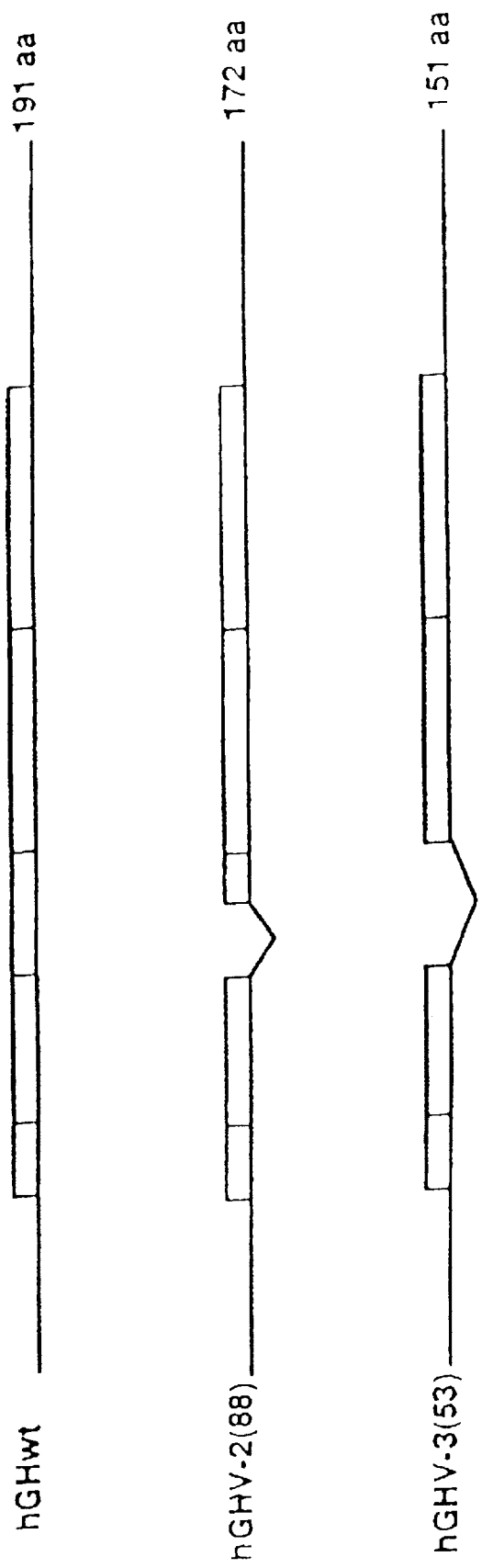
FIG. 1 is a schematic view of the polypeptides of wild-type human growth hormone, variant hGHV-2(88) and variant hGHV-3(53).

The invention further relates to polypeptides which are human growth hormone variants and which have the structure in FIGS. 1 and 2, as well as allelic variants thereof, and analogs, fragments and derivatives thereof which have the same function as the naturally occurring polypeptide. The variants are produced by alternative mRNA splicing of the exons of wild type hGH.

The present invention further relates to polypeptides encoded by the DNA contained in the clone deposited as ATCC number 75600 on Nov. 3, 1993 and ATCC number 75601 on Nov. 3, 1993, as well as analogs, fragments, derivatives and allelic variants thereof. These deposits will be maintained under the terms of the Budapest Treaty on the International Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with description of sequences herein. A license may be required to make, use or sell the deposited materials, and no such license is granted hereby.

The polypeptides of the present invention are preferably provided in an isolated form, and preferably are purified.

The term "isolated" means that the material is removed from its original environment (e.g., the natural environment if it is naturally occurring). For example, a naturally-occurring polynucleotide or polypeptide present in a living animal is not isolated, but the same polynucleotide or DNA or polypeptide, separated from some or all of the coexisting materials in the natural system, is isolated. Such polynucleotide could be part of a vector and/or such polynucleotide or polypeptide could be part of a composition, and still be isolated in that such vector or composition is not part of its natural environment.

In a preferred embodiment, the polypeptides are full length mature proteins or an allelic or glycosylated variant thereof. The polynucleotide may also encode a preprotein which is processed and secreted from mammalian cells as the mature protein.

The polynucleotide sequences of the present invention may encode for the mature form of the polypeptide or they may encode a leader sequence which facilitate expression of the polypeptides of the present invention. For example, the desired DNA sequences may be fused in the same reading frame to a DNA sequence which aids in expression of the polypeptide, for example a leader sequence which acts as a secretory sequence to control transportation of the polypeptides from the cell. The polynucleotides of the present invention may also be fused in frame to a marker sequence which allows for purification of the polypeptides of the present invention.

Thus, the polypeptide(s) of the present invention may be the mature form of the hGH splice variant(s) of the present invention; or may be in the form of a preprotein or prepolypeptide wherein the mature polypeptide includes a leader or secretory sequence; or may be in the form of a fusion protein wherein additional amino acids which aid in,-for example, purification of the polypeptide are fused to the mature or preprotein at either the 3' or 5' end thereof.

As hereinabove indicated, the present invention also includes variants of the polypeptides which are encoded by the DNA of FIG. 2 or variants of the DNA contained in the deposited clone, which retain the qualitative activity of such polypeptides which are hGHV-2(88) and hGHV-3(53), and which can function as an agonist and an antagonist for human growth hormone, respectively. The variant may be a substitutional variant, or an insertion variant or a deletional variant. Such variants can be naturally occurring allelic variants such as for example, those with different glycosylation patterns or substitution at the amino acid level or deletion at the amino acid level.

Such variants may also be produced by site specific mutagenesis. The substitutional variant may be a substituted conserved amino acid or a substituted non-conserved amino acid, and preferably a conserved amino acid.

Polynucleotides encoding polypeptides of the present invention may be obtained from pituitary tissue. They are structurally related to hGHwt and contain open reading frames encoding mature polypeptides of 172 and 151 amino acids. They are completely homologous to hGHwt except for the amino acids deleted as a result of alternative mRNA splicing. Variant hGHV-2(88) and variant hGHV-3(53) are generated by alternative splicing of the pre-mRNA where the splice donor site of exon-2 is fused to two alternate sites within exon-3 as shown in FIG. 1. This results in the removal of 57 and 120 nucleotides, respectively.

Amino acids comprising the leader sequence that are cleaved in the mature protein is shown (−26 to −1). The regions deleted by alternative splicing are shown by . . . , and correspond to amino acids 33 to 51 for hGHV-2(88) and 33 to 72 for hGHV-3(53), see FIG. 2.

Host cells are transformed with the expression vectors of this invention and cultured in conventional nutrient media modified as appropriate for inducing promoters, selecting transformants or amplifying the hGH splice variant(s) gene. The culture conditions, such as temperature, pH and the like, are those previously used with the host cell selected for expression, and will be apparent to the ordinarily skilled artisan. "Transformation" means introducing DNA into an organism so that the DNA is replicable, either as an extra-chromosomal element or by chromosomal integration. Unless indicated otherwise, the method used herein for transformation of the host cells is the method of Graham, F. and van der Eb, A., *Virology* 52: 456–457 (1973). However, other methods for introducing DNA into cells such as by nuclear injection or by protoplast fusion may also be used. If prokaryotic cells or cells which contain substantial cell wall constructions are used, the preferred method of transfection is calcium treatment using calcium chloride as described by Cohen, F. N. et al., *Proc. Natl. Acad. Sci.* (USA), 69:2110 (1972).

"Transfection" refers to the introduction of DNA into a host cell whether or not any coding sequences are ultimately expressed. Cells do not naturally take up DNA. Thus, a variety of technical "tricks" are utilized to facilitate gen transfer. Numerous methods of transfection are known to the ordinarily skilled artisan, for example, $CaPO_4$ and electroporation. (J. Sambrook, E. Fritsch, T. Maniatis, *Molecular Cloning: A Laboratory Manual*, Cold Spring Laboratory Press, 1989). Transformation of the host cell is the indicia of successful transfection.

The polynucleotide of the present invention may be employed for producing a polypeptide by recombinant techniques. Thus, for example, the polynucleotide sequence may be included in any one of a variety of vectors or plasmids for expressing a polypeptide. Such vectors include chromosomal, nonchromosomal and synthetic DNA sequences, e.g., derivatives of SV40; bacterial plasmids; phage DNA's; yeast plasmids; vectors derived from combinations of plasmids and phage DNAs, viral DNA such as vaccinia, adenovirus, fowl pox virus, and pseudorabies. However, any plasmid or vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the *E. coli*. lac or trp, the phage lambda PL promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain a gene to provide a phenotypic trait for selection of transformed host cells such as dihydrofolate reductase or neomycin resistance for eukaryotic cell culture, or such as tetracycline or ampicillin resistance in *E. coli*.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as *E. coli, Salmonella typhimurium*; fungal cells, such as yeast, animal cells such as CHO or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pBs, pQE-9 (Qiagen), phagescript, PsiX174, pBluescript SK, pBsKS, pNH8a, pNH16a, pNH18a, pNH46a (Stratagene); pTrc99A, pKK223-3, pKK233-3, pDR540, pRIT5 (Pharmacia). Eukaryotic: pWLneo, pSv2cat, pOG44, pXT1, pSG (Stratagene) pSVK3, pBPv, pMSG, pSVL (Pharmiacia). Also, any other plasmids and vectors may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described construct. The host cell can be a higher eukaryotic cell, such as a mammalian cell, or a lower eukaryotic cell, such as a yeast cell, or the host cell can be a procaryotic cell, such as a bacterial cell. Introduction of the construct into the host cell can be effected by calcium phosphate transfection, DEAE, dextran mediated transfection, or electroporation (Davis, L., Dibner, M., Battey, I., *Basic Methods in Molecular Biology*, 1986).

The constructs in host cells can be used in a conventional manner to produce the gene product coded by the recombinant sequence. Alternatively, the encoded polypeptide can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., *Molecular Cloning: A Laboratory Manual*, Second Edition, Cold Spring Harbor, N.Y., (1989), the disclosure of which is hereby incorporated by reference.

Transcription of a DNA encoding the polypeptides of the present invention by higher eukaryotes is increased by inserting an enhancer sequence into the vector. Enhancers are cis-acting elements of DNA, usually about from 10 to 300 bp, that act on a promotor to increase its transcription. Examples include the SV40 enhancer on the late side of the replication origin (bp 100 to 270), a cytomegalovirus early promotor enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These PBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

The human growth hormone variants of the present invention are purified from recombinant cell cultures including ammonium sulfate or ethanol precipitation, acid extraction, anion or cation exchange chromatography, affinity, chromatography, hydrophobic interaction chromatography, phosphocellulose chromatography, hydroxylapatite chromatography and lectin chromatography. It is preferred to have low concentrations (approximately 0.5–5 mM) of calcium ion present during purification. (Price et al., *J. Biol. Chem.* 244:917 (1969)).

Various mammalian cell culture systems can also be employed to express recombinant protein. Examples of mammalian expression systems include the COS-7 lines of monkey kidney fibroblasts, described by Gluzman, *Cell,* 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant protein produced in bacterial culture is usually isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture) of a polynucleotide sequence of the present invention. Depending upon the host employed in a recombinant production procedure, the polypeptides of the present invention may be glycosylated with mammalian or other eukaryotic carbohydrates or may be non-glycosylated. Polypeptides of the invention may also include an initial methionine amino acid residue (at position minus 1).

In addition to naturally occurring allelic forms of the polypeptide(s) the present invention also embraces analogs and fragments thereof, which function similarly to the naturally occurring allelic forms. Thus, for example, one or more of the amino acid residues of the polypeptide may be replaced by conserved amino acid residues.

hGHwt directs linear bone growth, has lactogenic activity and has also been shown to be involved in metabolic processes, such as lipid, nitrogen and carbohydrate metabolism, and has also been used to treat hip fractures in the elderly, chronic renal insufficiency, Turner's syndrome, cancer and AIDS.

Recent studies on wild-type human growth hormone have suggested that different regions of the molecule might be involved in directing these different activities. hGHV-2(88) binds to growth hormone receptors and produces a downstream response similar to that of hGHwt. In this way hGHV-2(88) is an agonist to hGHwt. Conversely, hGHV-3 (53) also binds to the receptors however, no such downstream response is produced. In this way, hGHV-3(53) acts to occupy receptor sites preventing activity normally associated with hGHwt. Therefore, hGHV-3(53) is an antagonist to hGHwt.

Accordingly, hGHV-2(88) could be used to treat hypopituitism by specifically stimulating production of hGHwt which then directs linear bone growth, since hypopituitism is characterized by abnormally slow growth and results in dwarfism. In the same manner, hGHV-2(88) could be used to increase milk production in cattle by stimulating lactogenic activity. hGHV-2(88) may also be used to treat obesity due to its possible lipolytic activity, to break down lipid in fat cells. In the same manner, hGHV-2(88) may be used to achieve the other functions of hGHwt, namely, carbohydrate metabolism to result in muscle production, treatment of hip fractures in the elderly, treatment of chronic renal insufficiency, Turner's syndrome, cancer and AIDS.

The human growth hormones splice variants of the present invention have fewer amino acids than the hGHwt. Accordingly, therefore, the human growth hormone variants may retain certain activities which are characteristic of hGHwt while not retaining others. Therefore the human growth hormone variants can be used to increase one function of hGHwt without increasing another. Accordingly, it is within the scope of this invention to identify and produce alternatively spliced human growth hormone variants which have specific functions of hGHwt while not having others.

hGHV-3(53) may be employed to treat hyperpituitism since hGHV-3(53) competes with hGHwt for the normal hGHwt receptor sites. By this action the normal functions of hGHwt are slowed or prevented altogether. hGHV-3(53) therefore is useful for treating gigantism and acromegaly which result from a hyperactive pituitary gland.

The polypeptides may also be employed in accordance with the present invention by expression of such polypeptides in vivo, which is often referred to as "gene therapy".

Thus, for example, cells may be transduced with a polynucleotide (DNA or RNA) encoding the polypeptides ex vivo with those transduced cells then being provided to a patient to be treated with the polypeptide. Such methods are well known in the art. For example, cells may be transduced by procedures known in the art by use of a retroviral particle containing RNA encoding the polypeptide of the present invention.

Similarly, transduction of cells may be accomplished in vivo for expression of the polypeptide in vivo, for example, by procedures known in the art. As known in the art, a producer cell for producing a retroviral particle containing RNA encoding the polypeptides of the present invention may be administered to a patient for transduction in vivo and expression of the polypeptides in vivo.

These and other methods for administering the polypeptides of the present invention by such methods should be apparent to those skilled in the art from the teachings of the present invention. For example, the expression vehicle for transducing cells may be other than a retrovirus, for example, an adenovirus which may be used to transduce cells in vivo after combination with a suitable delivery vehicle.

Further, the human growth hormone variants of the present invention can be utilized in the gene therapy methods described above if hyperactive or hypoactive pituitary function were diagnosed prenatally.

In the case where the polypeptides are prepared as a liquid formulation and administered by injection, preferably the solution is an isotonic salt solution containing 140 millimolar sodium chloride and 10 millimolar calcium at pH 7.4. The injection may be administered, for example, in a therapeutically effective amount, preferably in a dose of about 1 µg/kg body weight to about 5 mg/kg body weight daily, taking into account the routes of administration, symptoms, etc.

The polypeptide(s) of the present invention may be employed in combination with a suitable pharmaceutical carrier. Such compositions comprise a therapeutically effective amount of the protein, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptide of the present invention may be employed in conjunction with other therapeutic compounds.

When the human growth hormone variants of the present invention are used as a pharmaceutical, they can be given to mammals, in a suitable vehicle. When the polypeptides of the present invention are used as a pharmaceutical as described above, they are given, for example, in therapeutically effective doses of about 10 µg/kg body weight to about 5 mg/kg body weight once and about 5 µg/kg body weight to about 4 mg/kg body weight daily, taking into account the routes of administration, symptoms, etc.

Each of the cDNA sequences identified herein or a portion thereof can be used in numerous ways as polynucleotide reagents. The sequences can be used as diagnostic probes for the presence of a specific mRNA in a particular cell type. In addition, these sequences can be used as diagnostic probes suitable for use in genetic linkage analysis (polymorphisms).

The present invention is further directed to inhibiting hGHwt in vivo to reduce and/or eliminate its effect by use of antisense technology. Antisense technology can be used to control gene expression through triple helix formation or antisense RNA or DNA, both of which methods are based on the binding of a polynucleotide sequence to DNA or RNA. For example, the 5' coding portion of the polynucleotide sequence which encodes for hGHwt is used to design an antisense RNA oligonucleotide of from 10 to 40 base pairs in length. The RNA oligonucleotide hybridizes to the mRNA in vivo and blocks translation of the mRNA molecule into the mature hGHwt. (Antisense-Okano, *J. Neurochem.*, 56:560 (1991); *Oligodeoxynucleotides as Antisense Inhibitors of Gene Expression*, CRC Press, Boca Raton, Fla. (1988)). Similarly, a DNA oligonucleotide is designed to be complementary to a region of the gene involved in transcription, (triple helix—see Lee et al, *Nucl. Acids Res.*, 6:3073 (1979); Cooney et al, Science, 241:456 (1988); and Dervan et al, *Science*, 251: 1360 (1991), thereby preventing transcription and the production of hGHwt.

Alternatively, the oligonucleotides can be delivered to cells by procedures known in the art such that the antisense RNA or DNA may be expressed in vivo to inhibit production of hGHwt. Accordingly, antisense technology can be used to treat hyperpituitism.

The proteins, their fragments or other derivatives, or analogs thereof, or cells expressing them can be used as an immunogen to produce antibodies thereto. These antibodies can be, for example, polyclonal, monoclonal, chimeric, single chain, Fab fragments, or the product of an Fab expression library. Various procedures known in the art may be used for the production of polyclonal antibodies.

Antibodies generated against the polypeptide corresponding to a sequence of the present invention can be obtained by direct injection of the polypeptide into an animal or by administering the polypeptide to an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide. Moreover, a panel of such antibodies, specific to a large number of polypeptides, can be used to identify and differentiate such tissue.

For preparation of monoclonal antibodies, any technique which provides antibodies produced by continuous cell line cultures can be used. Examples include the hybridoma technique (Kohler and Milstein, 1975, *Nature*, 256:495-497), the trioma technique, the human B-cell hybridoma technique (Kozbor et al., 1983, *Immunology Today* 4:72), and the EBV-hybridoma technique to produce human monoclonal antibodies (Cole, et al., 1985, *Monoclonal Antibodies and Cancer Therapy*, Alan R. Liss, Inc., pp. 77–96).

Techniques described for the production of single chain antibodies (U.S. Pat. No. 4,946,778) can be adapted to produce single chain antibodies to immunogenic polypeptide products of this invention.

The antibodies can be used in methods relating to the localization and activity of the protein sequences of the invention, e.g., for imaging these proteins, measuring levels thereof in appropriate physiological samples and the like.

Antibodies specific to hGHwt may further be used as antagonists to inhibit the proper functioning of the polypeptide. In this manner, the antibodies may be used in a therapeutic manner, for example, to treat hyperpituitism.

Alternatively, an antagonist to hGHwt may be employed which bind to the receptors to which hGHwt normally binds. The antagonist is similar to an inactive form of the polypeptide and may be generated in ways similar to the ways in which the antibodies are generated. In this way the action of the hGHwt is prevented. Further, the antagonists detect the presence or absence of hGHwt and can therefore be used diagnostically to identify growth hormone related disorders, both during life and prenatally.

The present invention will be further described with reference to the following examples, however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid constriction, typically 5 to 50 μg of DNA are digested with 20 to 250 units of enzyme in a larger volume. Appropriate buffers and substrate amounts for particular restriction enzymes are specified by the manufacturer. Incubation times of about 1 hours at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., *Nucleic Acids Res.,* 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiaster bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

EXAMPLE 1

Bacterial Expression and Purification of the hGHV-2(88) and hGHV-3(53)

Figure 5:
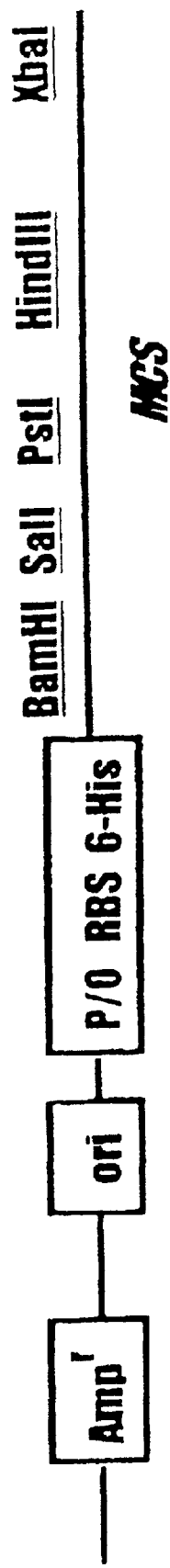
FIG. 5 is a schematic representation of the pQE-9 vector.

The DNA sequences encoding for HGHV-2(88) and hGHV-3(53) (ATCC No.s 75600 and 75601, respectively) are initially amplified using PCR oligonucleotide primers corresponding to the 5' and 3' end of the DNA sequence to synthesize insertion fragments. The 5' oligonucleotide primer has the sequence AGAGGATCCGCCATGGCTA-CAGGCTCCCGG (SEQ ID NO:7), contains a BamHI restriction enzyme site followed by 21 nucleotides of hGHV-2(88) and hGHV-3(53) coding sequence starting from the initiation codon; the 3' sequence contains complementary sequences to T7 promoter/sequence in the CDVA cloning vector, a translation stop codon and the hGHV-2(88) and hGHV-3(53) coding sequence. The restriction enzyme sites correspond to the restriction enzyme sites on the bacterial expression vector pQE-9. (Qiagen Inc., 9259 Eton Avenue, Chatsworth, Calif. 91311, Catalong No. 33093). The plasmid vector encodes antibiotic resistance ($Amp^r$), a bacterial origin of replication (ori), an IPTG-regulatable promoter/operator (P/O), a ribosome binding site (RBS), a 6-histidine tag (6-His) and restriction enzyme cloning sites. The pQE-9 vector was digested with BamHI and SalI and the insertion fragments were then ligated into the pQE-9 vector maintaining the reading frame initiated at the bacterial RBS. FIG. 5 shows a schematic representation of this arrangement. The ligation mixture was then used to transform the *E. coli* strain available from Qiagen under the trademark ml5/rep4. M15/rep4 contains multiple copies of the plasmid pREP4, which expresses the lacI repressor and also confers kanamycin resistance ($Kan^r$). Transformants are identified by their ability to grow on LB plates containing both Amp and Kan. Clones containing the desired constructs were grown overnight (O/N) in liquid culture in either LB media supplemented with both Amp (100 μg/ml) and Kan (25 μg/ml). The O/N culture is used to inoculate a large culture at a dilution of 1:100 to 1:250. The cells were grown to an optical density of 600 ($O.D.^{600}$) between 0.4 and 0.6. IPTG ("Isopropyl-B-D-thiogalacto pyranoside") was then added to a final concentration of 1 mM. IPTG induces by inactivating the lacI repressor, clearing the P/O leading to increased gene expression. Cells were grown an extra 3–4 hours. Cells were then harvested by centrifugation (20' at 6000×g). The cell pellet was solubilized in the chaotropic agent 6 Molar Guanidine HCL. After clarification, solubilized hGH variants were purified from this solution by chromatography on a Nickel-Chelate column under conditions that allow for tight binding by proteins containing the 6-His tag. (Hochuli, E. et al., *Genetic Engineering, Principle & Methods,* 12:87–98 (1990). hGHV-2(88) and hGHV-3(53) (95% pure) were eluted from the column in 6 molar guanidine HCL pH 5.0. Protein renaturation out of Guanidine HCl can be accomplished by several protocols. (Jaenicke, R. and Rudolph, R. *Protein Structure—A Practical Approach* IRL Press, New York (1990)). Initially, step dialysis is utilized to remove the GnHCl. Alternatively, the purified protein isolate from the Nichelate column can be bound to a second column over which a decreasing linear GnHCl gradient is run. The protein is allowed to renature while bound to the column and is subsequently eluted with GnHCl, pH 5.0. Finally, soluble protein is dialyzed against a storage buffer containing 140 mM NaCl, 20 mM NaPO4 and 10% w/v Glyconol.

Numerous modifications and variations of the present invention are possible in light of the above teachings and, therefore, within the scope of the appended claims, the invention may be practiced otherwise than as particularly described.

What is claimed is:

1. A method for the treatment of a patient having need of an agonist effect of human growth hormone, comprising administering to the patient a therapeutically effective amount of a polypeptide comprising an amino acid sequence consisting of residues −26 to +172 of SEQ ID NO:5.

2. The method of claim 1 wherein the amino acid sequence further comprises a heterologous polypeptide.

3. The method of claim 1 wherein the polypeptide is glycosylated.

4. The method of claim 1 wherein the polypeptide is fused to polyethylene glycol.

5. The method of claim 1 wherein the polypeptide is administered in combination with a pharmaceutically acceptable carrier.

6. The method of claim 5 wherein the administration is done by injection.

7. A method for the treatment of a patient having need of an agonist effect of human growth hormone, comprising administering to the patient a therapeutically effective amount of a polypeptide comprising an amino acid sequence selected from the group consisting of:

(a) residues 1 to 172 of SEQ ID NO:5; and (b) the amino acid sequence of a fragment of hGHV-2(88) which is an hGH agonist;

wherein the amino acid sequence further comprises a heterologous polypeptide.

8. The method of claim 7 wherein the amino acid sequence is (a).

9. The method of claim 7 wherein the amino acid sequence is (b).

10. A method for the treatment of a patient having need of an agonist effect of human growth hormone, comprising administering to the patient a therapeutically effective amount of a polypeptide comprising an amino acid sequence selected from the group consisting of:

(a) residues 1 to 172 of SEQ ID NO:5; and (b) the amino acid sequence of a fragment of hGHV-2(88) which is an hGH agonist;

wherein the polypeptide is glycosylated.

11. The method of claim 10 wherein the amino acid sequence is (a).

12. The method of claim 10 wherein the amino acid sequence is (b).

13. A method for the treatment of a patient having need of an agonist effect of human growth hormone, comprising administering to the patient a therapeutically effective amount of a polypeptide comprising an amino acid sequence selected from the group consisting of:

(a) residues 1 to 172 of SEQ ID NO:5; and (b) the amino acid sequence of a fragment of hGHV-2(88) which is an hGH agonist;

wherein the polypeptide is fused to polyethylene glycol.

14. The method of claim 13 wherein the amino acid sequence is (a).

15. The method of claim 13 wherein the amino acid sequence is (b).

16. A method for the treatment of a patient having need of an agonist effect of human growth hormone, administering to the patient a therapeutically effective amount of a polypeptide comprising an amino acid sequence selected from the group consisting of:
   (a) residues 1 to 172 of SEQ ID NO:5; and
   (b) the amino acid sequence of a fragment of hGHV-2(88) which is an hGH agonist;
wherein the polypeptide is administered in combination with a pharmaceutically acceptable carrier.

17. The method of claim 16 wherein the amino acid sequence is (a).

18. The method of claim 16 wherein the amino acid sequence is (b).

19. A method for the treatment of a patient having need of an agonist effect of human growth hormone, comprising administering to the patient a therapeutically effective amount of a polypeptide comprising an amino acid sequence selected from the consisting of:
   (a) residues 1 to 172 of SEQ ID NO:5; and
   (b) the amino acid sequence of a fragment of hGHV-2(88) which is an hGH agonist;
wherein administration is done by injection.

20. The method of claim 19 wherein the amino acid sequence is (a).

21. The method of claim 19 wherein the amino acid sequence is (b).

22. A method for the treatment of a patient having need of an agonist effect of human growth hormone, comprising administering to the patient a therapeutically effective amount of a polypeptide comprising an amino acid sequence selected from the group consisting of:
   (a) the amino acid sequence of the mature protein encoded by the human cDNA contained in ATCC Deposit No. 75600;
   (b) the amino acid sequence of the complete polypeptide encoded by the human cDNA contained in ATCC Deposit No. 75600; and
   (c) the amino acid sequence of a fragment of the mature protein encoded by the human cDNA contained in ATCC Deposit No. 75600, wherein said fragment is an hGH agonist;
wherein the amino acid sequence further comprises a heterologous polypeptide.

23. The method of claim 22 wherein the amino acid sequence is (a).

24. The method of claim 22 wherein the amino acid sequence is (b).

25. The method of claim 22 wherein the amino acid sequence is (c).

26. A method for the treatment of a patient having need of an agonist effect of human growth hormone, comprising administering to the patient a therapeutically effective amount of a polypeptide comprising an amino acid sequence selected from the group consisting of:
   (a) the amino acid sequence of the mature protein encoded by the human cDNA contained in ATCC Deposit No. 75600;
   (b) the amino acid sequence of the complete polypeptide encoded by the human cDNA contained in ATCC Deposit No. 75600; and
   (c) the amino acid sequence of a fragment of the mature protein encoded by the human cDNA contained in ATCC Deposit No. 75600, wherein said fragment is an hGH agonist;
wherein the polypeptide is glycosylated.

27. The method of claim 26 wherein the amino acid sequence is (a).

28. The method of claim 26 wherein the amino acid sequence is (b).

29. The method of claim 26 wherein the amino acid sequence is (c).

30. A method for the treatment of a patient having need of an agonist effect of human growth hormone, comprising administering to the patient a therapeutically effective amount of a polypeptide comprising an amino acid sequence selected from the group consisting of:
   (a) the amino acid sequence of the mature protein encoded by the human cDNA contained in ATCC Deposit No. 75600;
   (b) the amino acid sequence of the complete polypeptide encoded by the human cDNA contained in ATCC Deposit No. 75600; and
   (c) the amino acid sequence of a fragment of the mature protein encoded by the human cDNA contained in ATCC Deposit No. 75600, wherein said fragment is an hGH agonist;
wherein the polypeptide is fused to polyethylene glycol.

31. The method of claim 30 wherein the amino acid sequence is (a).

32. The method of claim 30 wherein the amino acid sequence is (b).

33. The method of claim 30 wherein the amino acid sequence is (c).

34. A method for the treatment of a patient having need of an agonist effect of human growth hormone, comprising administering to the patient a therapeutically effective amount of a polypeptide comprising an amino acid sequence selected from the group consisting of:
   (a) the amino acid sequence of the mature protein encoded by the human cDNA contained in ATCC Deposit No. 75600;
   (b) the amino acid sequence of the complete polypeptide encoded by the human cDNA contained in ATCC Deposit No. 75600; and
   (c) the amino acid sequence of a fragment of the mature protein encoded by the human cDNA contained in ATCC Deposit No. 75600, wherein said fragment is an hGH agonist;
wherein the polypeptide is administered in combination with a pharmaceutically acceptable carrier.

35. The method of claim 34 wherein the amino acid sequence is (a).

36. The method of claim 34 wherein the amino acid sequence is (b).

37. The method of claim 34 wherein the amino acid sequence is (c).

38. A method for the treatment of a patient having need of an agonist effect of human growth hormone, comprising administering to the patient a therapeutically effective amount of a polypeptide comprising an amino acid sequence selected from the group consisting of:
   (a) the amino acid sequence of the mature protein encoded by the human cDNA contained in ATCC Deposit No. 75600;
   (b) the amino acid sequence of the complete polypeptide encoded by the human cDNA contained in ATCC Deposit No. 75600; and
   (c) the amino acid sequence of a fragment of the mature protein encoded by the human cDNA contained in ATCC Deposit No. 75600, wherein said fragment is an hGH agonist;
wherein the administration is done by injection.

39. The method of claim 38 wherein the amino acid sequence is (a).

40. The method of claim 38 wherein the amino acid sequence is (b).

41. The method of claim 38 wherein the amino acid sequence is (c).

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 654 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
ATGGCTGCAG GCTCCCGGAC GTCCCTGCTC CTGGCTTTTG GCCTGCTCTG CCTGTCCTGG    60
CTTCAAGAGG GCAGTGCCTT CCCAACCATT CCCTTATCCA GGCTTTTTGA CAACGCTATG   120
CTCCGCGCCC GTCGCCTGTA CCAGCTGGCA TATGACACCT ATCAGGAGTT TGAAGAAGCC   180
TATATCCTGA AGGAGCAGAA GTATTCATTC CTGCAGAACC CCCAGACCTC CCTCTGCTTC   240
TCAGAGTCTA TTCCAACACC TTCCAACAGG GTGAAAACGC AGCAGAAATC TAACCTAGAG   300
CTGCTCCGCA TCTCCCTGCT GCTCACTCAG TCATGGCTGG AGCCCGTGCA GCTCCTCAGG   360
AGCGTCTTCG CCAACAGCCT GGTGTATGGC GCCTCGGAGA GCAACGTCTA TCGCCACCTG   420
AAGGACCTAG ACGAAGGCAT CCAAACGCTG ATGTGGAGGC TGGAAGATGG CAGCCCCCGG   480
ACTGGGCAGA TCTTCAATCA GTCCTACAGC AAGTTTGACA CAAAATCGCA CAACGATGAC   540
GCACTGCTCA AGAACTACGG GCTGCTCTAC TGCTTCAGGA AGGACATGGA CAAGGTCGAG   600
ACATTCCTGC GCATCGTGCA GTGCCGCTCT GTGGAGGGCA GCTGTGGCTT CTAG         654
```

(2) INFORMATION FOR SEQ ID NO:2:

(i) SEQUENCE CHARACTERISTICS:
      (A) LENGTH: 597 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
ATGGCTGCAG GCTCCCGGAC GTCCCTGTCT CTGGCTTTTG GCTCGCTCTG CCTGTCCTGG    60
CTTCAAGAGG GCAGTGCCTT CCCAACCATT CCCTTATCCA GGCTTTTTGA CAACGCTATG   120
CTCCGCGCCC GTCGCCTGTA CCAGCTGGCA TATGACACCT ATCAGGAGTT TTCCCTCTGC   180
TTCTCAGAGT CTATTCCAAC ACCTTCCAAC AGGGTGAAAA CGCAGCAGAA ATCTAACCTA   240
GAGCTGCTCC GCATCTCCCT GCTGCTCACT CAGTCATGGC TGGAGCCCGT GCAGCTCCTC   300
AGGAGCGTCT TCGCCAACAG CCTGGTGTAT GGCGCCTCGG AGAGCAACGT CTATCGCCAC   360
CTGAAGGACC TAGAGGAAGG CATCCAAAGC CTGATGTGGA GGCTGGAAGA TGGCAGCCCC   420
CGGACTGGGC AGATCTTCAA TCAGTCCTAC AGCAAGTTTG ACACAAAATC GCACAACGAT   480
GACGCACTGC TCAAGAACTA CGGGCTGCTC TACTGCTTCA GGAAGGACAT GGACAAGGTC   540
GAGACATTCC TGCGCATCGT GCAGTGCCGC TCTGTCGAGG GCAGCTGTGG CTTCTAG     597
```

(2) INFORMATION FOR SEQ ID NO:3:

(i) SEQUENCE CHARACTERISTICS:

(A) LENGTH: 534 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

ATGGCTGCAG GCTCCCGGAC GTCCCTGCTC CTGGCTTTTG GCCTGCTCTG CCTGTCCTGG      60

CTTCAAGAGG GCAGTGCCTT CCCAACCATT CCCTTATCCA GGCTTTTTGA CAACGCTATG     120

CTCCGCGCCC GTCGCCTGTA CCAGCTGGCA TATGACACCT ATCAGGAGTT TAACCTAGAG     180

CTGCTCCGCA TCTCCCTGCT GCTCACTCAG TCATGGCTGG AGCCCGTGCA GCTCCTCAGG     240

AGCGTCTTCG CCAACAGCCT GGTGTATGGC GCCTCGGACA GCAACGTCTA TCGCCACCTG     300

AAGGACCTAG AGGAAGGCAT CCAAACGCTG ATGTGGAGGC TGGAAGATGG CAGCCCCCGG     360

ACTGGGCAGA TCTTCAATCA GTCCTACAGC AAGTTTGACA CAAAATCGCA CAACGATGAC     420

GCACTGCTCA AGAACTACGG GCTGCTCTAC TGCTTCAGGA AGGACATGGA CAAGGTCGAG     480

ACATTCCTGC GCATCGTGCA GTGCCGCTCT GTGGAGGGCA GCTGTGGCTT CTAG           534

(2) INFORMATION FOR SEQ ID NO:4:

(i) SEQUENCE CHARACTERISTICS:
        (A) LENGTH:   217 AMINO ACIDS
        (B) TYPE:   AMINO ACID
        (C) STRANDEDNESS:
        (D) TOPOLOGY:   LINEAR (ii) MOLECULE TYPE:   PROTEIN (xi) SEQUENCE DESCRIPTION:   SEQ ID NO:4:

Met Ala Ala Gly Ser Arg Thr Ser Leu Leu Leu Ala Phe Gly Leu
-25                 -20                 -15

Leu Cys Leu Ser Trp Leu Gln Glu Gly Ser Ala Phe Pro Thr Ile
-10                  -5                   1

Pro Leu Ser Arg Leu Phe Asp Asn Ala Ser Leu Arg Ala His Arg
 5                  10                  15

Leu His Gln Leu Ala Phe Asp Thr Tyr Gln Glu Phe Glu Glu Ala
20                  25                  30

Tyr Ile Pro Lys Glu Gln Lys Tyr Ser Phe Leu Gln Asn Pro Gln
35                  40                  45

Thr Ser Leu Cys Phe Ser Glu Ser Ile Pro Thr Pro Ser Asn Arg
50                  55                  60

Glu Glu Thr Gln Gln Lys Ser Asn Leu Glu Leu Leu Arg Ile Ser
65                  70                  75

Leu Leu Leu Ile Gln Ser Trp Leu Glu Pro Val Gln Phe Leu Arg
80                  85                  90

Ser Val Phe Ala Asn Ser Leu Val Tyr Gly Ala Ser Asp Ser Asn
95                  100                 105

Val Tyr Asp Leu Leu Lys Asp Leu Glu Glu Gly Ile Gln Thr Leu
110                 115                 120

Met Gly Arg Leu Glu Asp Gly Ser Pro Arg Thr Gly Gln Ile Phe
125                 130                 135

Lys Gln Thr Tyr Ser Lys Phe Asp Thr Asn Ser His Asn Asp Asp
140                 145                 150

Ala Leu Leu Lys Asn Tyr Gly Leu Leu Tyr Cys Phe Arg Lys Asp
155                 160                 165

```
Met Asp Lys Val Glu Thr Phe Leu Arg Ile Val Gln Cys Arg Ser
170                 175                 180

Val Glu Gly Ser Cys Gly Phe
185                 190

(2) INFORMATION FOR SEQ ID NO:5:

(i) SEQUENCE CHARACTERISTICS:
        (A) LENGTH: 198 AMINO ACIDS
        (B) TYPE:   AMINO ACID
        (C) STRANDEDNESS:
        (D) TOPOLOGY: LINEAR (ii) MOLECULE TYPE:  PROTEIN (xi) SEQUENCE DESCRIPTION: SEQ ID NO:5:

Met Ala Ala Gly Ser Arg Thr Ser Leu Leu Leu Ala Phe Gly Leu
-25                 -20                 -15

Leu Cys Leu Ser Trp Leu Gln Glu Gly Ser Ala Phe Pro Thr Ile
-10                 -5                  1

Pro Leu Ser Arg Leu Phe Asp Asn Ala Ser Leu Arg Ala His Arg
5                   10                  15

Leu His Gln Leu Ala Phe Asp Thr Tyr Gln Glu Phe Ser Leu Cys
20                  25                  30

Phe Ser Glu Ser Ile Pro Thr Pro Ser Asn Arg Glu Glu Thr Gln
35                  40                  45

Gln Lys Ser Asn Leu Glu Leu Leu Arg Ile Ser Leu Leu Leu Ile
50                  55                  60

Gln Ser Trp Leu Glu Pro Val Gln Phe Leu Arg Ser Val Phe Ala
65                  70                  75

Asn Ser Leu Val Tyr Gly Ala Ser Asp Ser Asn Val Tyr Asp Leu
80                  85                  90

Leu Lys Asp Leu Glu Glu Gly Ile Gln Thr Leu Met Gly Arg Leu
95                  100                 105

Glu Asp Gly Ser Pro Arg Thr Gly Gln Ile Phe Lys Gln Thr Tyr
110                 115                 120

Ser Lys Phe Asp Thr Asn Ser His Asn Asp Asp Ala Leu Leu Lys
125                 130                 135

Asn Tyr Gly Leu Leu Tyr Cys Phe Arg Lys Asp Met Asp Lys Val
140                 145                 150

Glu Thr Phe Leu Arg Ile Val Gln Cys Arg Ser Val Glu Gly Ser
155                 160                 165

Cys Gly Phe
170

(2) INFORMATION FOR SEQ ID NO:6:

(i) SEQUENCE CHARACTERISTICS:
        (A) LENGTH: 177 AMINO ACIDS
        (B) TYPE:   AMINO ACID
        (C) STRANDEDNESS:
        (D) TOPOLOGY: LINEAR (ii) MOLECULE TYPE:  PROTEIN (xi) SEQUENCE DESCRIPTION: SEQ ID NO:6:

Met Ala Ala Gly Ser Arg Thr Ser Leu Leu Leu Ala Phe Gly Leu
-25                 -20                 -15

Leu Cys Leu Ser Trp Leu Gln Glu Gly Ser Ala Phe Pro Thr Ile
-10                 -5                  1

Pro Leu Ser Arg Leu Phe Asp Asn Ala Ser Leu Arg Ala His Arg
```

```
                5                    10                   15
Leu His Gln Leu Ala Phe Asp Thr Tyr Gln Glu Phe Asn Leu Glu
20                       25                   30

Leu Leu Arg Ile Ser Leu Leu Ile Gln Ser Trp Leu Glu Pro
35                       40                   45

Val Gln Phe Leu Arg Ser Val Phe Ala Asn Ser Leu Val Tyr Gly
50                       55                   60 ala Ser Asp Ser Asn Val Tyr Asp Leu Leu Lys Asp Leu Glu Glu
65                       70                   75

Gly Ile Gln Thr Leu Met Gly Arg Leu Glu Asp Gly Ser Pro Arg
80                       85                   90

Thr Gly Gln Ile Phe Lys Gln Thr Tyr Ser Lys Phe Asp Thr Asn
95                       100                  105

Ser His Asn Asp Asp Ala Leu Leu Lys Asn Tyr Gly Leu Leu Tyr
110                      115                  120

Cys Phe Arg Lys Asp Met Asp Lys Val Glu Thr Phe Leu Arg Ile
125                      130                  135

Val Gln Cys Arg Ser Val Glu Gly Ser Cys Gly Phe
140                      145                  150

(2) INFORMATION FOR SEQ ID NO:7:

(i) SEQUENCE CHARACTERISTICS:
        (A) LENGTH:  30 BASE PAIRS
        (B) TYPE:  NUCLEIC ACID
        (C) STRANDEDNESS:  SINGLE
        (D) TOPOLOGY:  LINEAR (ii) MOLECULE TYPE:  Oligonucleotide (xi) SEQUENCE DESCRIPTION:  SEQ ID NO:7:

AGAGGATCCG CCATGGCTAC AGGCTCCCGG                                  30
```